(12) United States Patent
Mansfield et al.

(10) Patent No.: US 7,510,720 B1
(45) Date of Patent: Mar. 31, 2009

(54) VACCINE TO CONTROL EQUINE PROTOZOAL MYELOENCEPHALITIS IN HORSES

(75) Inventors: Linda S. Mansfield, Bath, MI (US); Mary G. Rossano, Mason, MI (US); Alice J. Murphy, St. Johns, MI (US); Ruth A. Vrable, Williamston, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 1947 days.

(21) Appl. No.: 09/670,096

(22) Filed: Sep. 26, 2000

Related U.S. Application Data

(62) Division of application No. 09/513,086, filed on Feb. 24, 2000, now Pat. No. 7,419,668.

(60) Provisional application No. 60/152,193, filed on Sep. 2, 1999.

(51) Int. Cl.
*A61K 39/002* (2006.01)
*A61K 38/00* (2006.01)

(52) U.S. Cl. ............... 424/265.1; 424/184.1; 424/178.1; 514/2; 514/44

(58) Field of Classification Search ............... 424/130.1, 424/134.1, 139.1, 141.1, 151.1, 178.1, 184.1, 424/185.1, 191.1, 192.1, 265.1, 269.1; 435/69.7, 435/70.21, 70.1, 71.1, 455; 536/23.4; 514/2–21, 514/44; 436/518, 523, 528, 543
See application file for complete search history.

(56) References Cited

U.S. PATENT DOCUMENTS

| | | | |
|---|---|---|---|
| 4,486,530 A | 12/1984 | David et al. | |
| 4,786,589 A | 11/1988 | Rounds | |
| 5,169,789 A | 12/1992 | Bernstein | |
| 5,223,424 A | 6/1993 | Cochran et al. | |
| 5,229,293 A | 7/1993 | Matsuura et al. | |
| 5,266,313 A | 11/1993 | Esposito et al. | |
| 5,338,683 A | 8/1994 | Paoletti | |
| 5,494,807 A | 2/1996 | Paoletti et al. | |
| 5,559,041 A | 9/1996 | Kang et al. | |
| 5,561,064 A | 10/1996 | Marquet et al. | |
| 5,580,859 A | 12/1996 | Felgner | |
| 5,585,100 A | 12/1996 | Mond et al. | |
| 5,589,384 A | 12/1996 | Liscombe et al. | |
| 5,589,466 A | 12/1996 | Felgner et al. | |
| 5,620,845 A | 4/1997 | Gould et al. | |
| 5,656,448 A | 8/1997 | Kang et al. | |
| 5,693,761 A | 12/1997 | Queen et al. | |
| 5,693,762 A | 12/1997 | Queen et al. | |
| 5,695,928 A | 12/1997 | Stewart | |
| 5,703,055 A | 12/1997 | Felgner et al. | |
| 5,725,863 A | 3/1998 | Daniels et al. | |
| 5,728,587 A | 3/1998 | Kang et al. | |
| 5,731,188 A | 3/1998 | Cochran et al. | |
| 5,741,696 A | 4/1998 | Cochran et al. | |
| 5,747,476 A | 5/1998 | Russell et al. | |
| 5,800,821 A | 9/1998 | Acheson et al. | |
| 5,830,893 A | 11/1998 | Russell | |
| 5,883,095 A | 3/1999 | Granstrom et al. | |
| 5,925,622 A | 7/1999 | Rossignol et al. | |
| 5,928,913 A | 7/1999 | Efstathiou et al. | |
| 5,935,591 A | 8/1999 | Rossignol et al. | |
| 5,935,777 A | 8/1999 | Moyer et al. | |
| 5,977,322 A | 11/1999 | Marks et al. | |
| 6,344,337 B1 * | 2/2002 | Mansfield et al. | ............ 435/7.2 |
| 6,489,148 B1 * | 12/2002 | Mansfield et al. | ........... 435/183 |

OTHER PUBLICATIONS

Liang et al 1998 Infection and Immunity; 66 (5) 1834-1838.*
Fenger et al, JAVMA, 1997, 210/7:923-927.*
Granstrom et al, J. Vet. Diagn. Invest., 1993, 5:88-90.*
Rossano et al, J. Vet. Diagn. Invest., 2000, 12:28-32.*
Vatistas et al, Equine Practice, 1999, 21/5:18-21.*
Cutler et al, Vet. Parasitology, 2001, 95:197-210.*
Rossano et al, Preventive Vet. Medicine, 2001, 48:113-128.*
Rossano et al, JAVMA, 2002, 221/4:511-514.*
Rossano et al, Pr ventive Vet. Medicine, 2003, 57:7-13.*
Liang et al 1998 (Infection and Immunity; 66 (5) 1834-1838).*
Liang et al 1997 (Analytical Biochemistry; 250 (1) 61-5).*
Harlow and Lane 1988 (IDS: Antibodies; especially chapter 5 and 6 Cold Spring Harbor).*
McKay et al., Veterinary Clinics of North America: Equine Practice for Practicing Vets. 13(1):79-96 (1997).

(Continued)

*Primary Examiner*—Robert B Mondesi
*Assistant Examiner*—Padma V Baskar
(74) *Attorney, Agent, or Firm*—Ian C. McLeod

(57) ABSTRACT

The present invention provides vaccines and methods for making the vaccines that actively or passively protect an equid or other animal against Sarcocystis neurona. In particular, the present invention provides vaccines that provide active immunity which comprise a polypeptide or DNA vaccine that contains or expresses at least one epitope of an antigen that has an amino acid sequence substantially similar to a unique 16 (±4) kDa antigen and/or 30 (±4) kDa antigen of Sarcocystis neurona. The present invention further provides a vaccine that provides passive immunity to Sarcocystis neurona comprising polyclonal or monoclonal antibodies against at least one epitope of an antigen substantially similar to a unique 16 (±4) kDa antigen and/or 30 (±4) kDa antigen of Sarcocystis neurona.

2 Claims, No Drawings

OTHER PUBLICATIONS

Blythe et al., J. Am. Vet. Med. Assoc. 210: 525-527 (1997).
Saville et al., J. Am. Vet. Assoc. 210: 519-524 (1997).
Bentz et al., J. Am. Vet. Med. Assoc. 210: 517-518 (1997).
Granstom et al., J. Vet. Diag. Invest. 5: 88-90 (1993).
Fenger et al., Vet. Parasitol. 68: 199-213 (1997).
Martenuik et al., Proceedings of the Conference of Research Workers in Animal Diseases, Chicago, IL (1997).
Motin et al., Infect. Immun. 64: 4313-4318 (1996).
Motin et al., Infect. Immun. 64: 3021-3029 (1995).
Engvall et al., Immunochem. 8: 871 (1971).
Ljunggren et al., J. Immunol. Methods 104: 7-14 (1987).
Kemeny et al., J. Immunol. Methods 87: 45-50 (1986).
Antibodies, A Laboratory Manual, eds. Harlow and Lane, Cold Spring Harbor Lab. Press, Cold Spring Harbor, New York, (1988).
Sloss et al., In Veterinary Clinical Parasitology, Iowa State Univ. Press, Ames, Iowa, (1994) p. 198.
Marsh et al., J. Parasitology 83: 1189-1192 (1997).
Speer et al., J. Protozoology 33: 486-490 (1986).

* cited by examiner

VACCINE TO CONTROL EQUINE PROTOZOAL MYELOENCEPHALITIS IN HORSES

CROSS-REFERENCE TO RELATED APPLICATION

This application is a divisional of application(s) application Ser. No. 09/513,086 filed on Feb. 24, 2000 now U.S. Pat. No. 7,419,668 application claims the benefit of U.S. Provisional Patent Application Ser. No. 60/152,193, filed on Sep. 2, 1999.

BACKGROUND OF THE INVENTION (1) Field of the Invention

The present invention relates to vaccines and methods for making the vaccines that actively or passively protect an equid or other animal against *Sarcocystis neurona*. In particular, the present invention relates to vaccines that provide active immunity which comprise a polypeptide or DNA vaccine that contains or expresses at least one epitope of an antigen that has an amino acid sequence substantially similar to a unique 16 (±4) kDa antigen and/or 30 (±4) kDa antigen of *Sarcocystis neurona*. The present invention further relates to a vaccine that provides passive immunity to *Sarcocystis neurona* comprising polyclonal or monoclonal antibodies against at least one epitope of an antigen substantially similar to a unique 16 (±4) kDa antigen and/or 30 (±4) kDa antigen of *Sarcocystis neurona*.

(2) Description of Related Art

Equine protozoal myeloencephalitis (EPM) is an emerging neurological disease caused by the protozoan parasite *Sarcocystis neurona*. In recent years, EPM has caused significant health, economic, and emotional costs to horses and their owners (reviewed by McKay et al., Veterinary Clinics of North America 13: 79-96 (1997). Opossums have been implicated as the natural reservoir of *Sarcocystis neurona* because the sexual stages of the parasite occur in the intestines of the opossum and the sporocysts are passed in the feces of the opossum. Horses accidentally eat the opossum feces containing the sporocysts when they are grazing; however, because *Sarcocystis neurona* does not appear to form mature tissue cysts in equids, equids are considered to be dead end hosts. Because opossums are ubiquitous in the United States, large numbers of equids are exposed to this parasite: approximately 50 to 60% of the horses nationwide (Blythe et al., J. Am. Vet. Med. Assoc. 210: 525-527 (1997), Saville et al., J. Am. Vet. Assoc. 210: 519-524 (1997), Bentz et al., J. Am. Vet. Med. Assoc. 210: 517-518 (1997)).

Currently, there are no adequate diagnostic tests for determining whether an equid is currently infected with *Sarcocystis neurona*. A Western blot test was developed to detect antibodies to *Sarcocystis neurona* in cerebrospinal fluid of equids suspected of having EPM; however, these Western blot assays have not been reliable in predicting the presence of *Sarcocystis neurona* due to the prevalence in equids of cross-reacting antibodies to other *Sarcocystis* species (Granstom et al. J. Vet. Diag. Invest. 5: 88-90 (1993), Fenger et al., Vet. Parasitol. 68: 199-213 (1997), Bentz et al., ibid., Saville et al., ibid., Blythe et al., ibid.).

Currently, there are no vaccines to protect equids from the parasite, and current treatment regimes are effective in only about 50% of the equids (Martenuik et al., Proceedings, Conference of Research Workers on Animal Disease, Chicago, Ill., 1997). However, these studies on treatment efficacy were based on a low number of horses. The U.S. Department of Agriculture (USDA), Animal and Plant Health Inspection Service (APHIS), National Animal Health Monitoring System (NAHMS) of the Needs Assessment Survey (NAS) has designated EPM as one of the top two infectious diseases of national importance to the horse industry. Among veterinarians and race horse owners, EPM has been ranked as the leading health care concern. In particular, 58% of the race horse owners ranked EPM as the top health care concern.

Since there are no vaccines for EPM and EPM is a significant health concern of the equine industry, considerable effort has been directed towards developing therapeutic methods for treating EPM. For example, U.S. Pat. No. 5,935,591 to Rossignol et al. describes using thiazolides as a treatment for EPM; U.S. Pat. No. 5,883,095 to Granstrom et al. describes using triazine-based anti-coccidials as a treatment for EPM; U.S. Pat. No. 5,830,893 to Russel describes using triazinediones as a treatment for EPM; U.S. Pat. No. 5,747,476 to Russel describes using a combination of pyrimethamine and a sulfonamide, preferably sulfadiazine in the absence of known therapeutic amounts of trimethoprim as a treatment for EPM; and U.S. Pat. No. 5,925,622 to Rossignol et al. describes using aryl glucuronide of 2-hydroxy-N-(5-nitro-2-thiazolyl) benzamide as a treatment for EPM.

Treatment for EPM is expensive and cumbersome because of the long duration required to achieve positive results. Because many horses cannot be successfully treated, economically and emotionally valuable animals have been lost to EPM. However, the extent of EPM's economic impact is even greater because of the large sums of money spent by horse owners for treating lame horses which have been incorrectly diagnosed with EPM, for giving prophylactic treatments that have no scientific basis, and for finding positive post-race drug test results.

EPM has been the cause of hysteria in the equid industry. The small amount of scientific data available on EPM supports a high exposure rate of equids, but there are no data available that document the rate of clinical disease resulting from exposure to the parasite. Because of this, horse owners and veterinarians assume that the rate of clinical disease is high. As a result, several alarming consequences have arisen. Equids with lameness or other neurological diseases are being misdiagnosed as having EPM. People whose livelihoods depend on horses are resorting to medicating all their horses all of the time with antimicrobials. This approach to treating EPM is very widespread in the racing industry. However, this indiscriminate use of antimicrobials has the potential of leading to resistant bacteria such as *Salmonella*, *E. coli*, etc. which will then enter the environment and pose a risk for humans and animals. Thus, the repercussions of EPM may extend beyond a disease that merely affects the horse industry. All of the repercussions of EPM are expensive, decrease the value realized to the U.S. equid industry, and raise the specter of a public health problem of immense proportions.

Therefore, there is a need for a treatment of EPM that is effective and has little or no side-effects.

SUMMARY OF THE INVENTION

The present invention provides vaccines and methods for making the vaccines that protect an equid or other animal host against *Sarcocystis neurona*. In particular, the present invention provides a vaccine that elicits active immunity against *Sarcocystis neurona* which contains at least one epitope of a 16 (±4) kDa antigen and/or 30 (±4) kDa antigen of *Sarcocystis neurona*. The present invention further provides a DNA vaccine that elicits active immunity against *Sarcocystis neu-*

*rona* comprising a DNA encoding at least one epitope of a 16 (±4) kDa antigen and/or 30 (±4) kDa antigen of *Sarcocystis neurona*.

The present invention further provides a vaccine for providing passive immunity to a *Sarcocystis neurona* infection comprising antibodies which are against at least one epitope of at 16 (±4) kDa antigen and/or 30 (±4) kDa antigen of *Sarcocystis neurona*. In particular, a vaccine wherein the antibodies are selected from the group consisting of polyclonal antibodies and monoclonal antibodies against a 16 (±4) kDa antigen and/or 30 (±4) kDa antigen of *Sarcocystis neurona*. In a preferred embodiment of the vaccine, the vaccine is provided in a pharmaceutically accepted carrier.

Further, the present invention further provides a vaccine for active immunization of an equid against a *Sarcocystis neurona* infection comprising an antigen containing at least one epitope of a 16 (±4) kDa antigen and/or 30 (±4) kDa antigen of *Sarcocystis neurona*. In one embodiment of the present invention, the antigen is a recombinant polypeptide produced in a plasmid in a microorganism other than *Sarcocystis neurona*, preferably, in an *E. coli*. In a preferred embodiment, the vaccine is provided in a pharmaceutically accepted carrier.

Further, the present invention provides for a vaccine wherein the 16 (±4) kDa antigen and/or 30 (±4) kDa antigen of *Sarcocystis neurona* antigen is provided as a fusion polypeptide wherein an amino end and/or a carboxyl end of the antigen is fused to all or a portion of a polypeptide that facilitates the isolation of the antigen from the microorganism in which the antigen is produced. In a preferred embodiment, the polypeptide is selected from the group consisting of glutathione S-transferase, protein A, maltose binding protein, and polyhistidine.

The present invention also provides a vaccine for protecting an equid from a *Sarcocystis neurona* infection comprising a DNA that encodes at least one epitope of a 16 (±4) kDa antigen and/or 30 (±4) kDa antigen of *Sarcocystis neurona*. In a preferred embodiment, the DNA is operably linked to a promoter to enable transcription of the DNA in the cell of an equid. Preferably, the vaccine is provided in a pharmaceutically accepted carrier.

The present invention further provides a method for vaccinating an equid against a *Sarcocystis neurona* infection comprising: (a) providing a recombinant antigen of the *Sarcocystis neurona* produced from a microorganism culture wherein the microorganism contains a DNA that encodes a 16 (±4) kDa antigen and/or 30 (±4) kDa antigen of *Sarcocystis neurona*; and (b) vaccinating the equid. Preferably, the vaccine is in a pharmaceutically accepted carrier.

In a preferred embodiment of the method, the recombinant antigen is a fusion polypeptide which is fused at the amino terminus and/or carboxyl terminus to a polypeptide that facilitates the isolation of the recombinant antigen. In particular, the polypeptide is all or a portion of the polypeptide selected from the group consisting of glutathione S-transferase, protein A, maltose binding protein, and polyhistidine. Further, the method includes producing the antigen from a DNA which is in a plasmid in a microorganism wherein the DNA is operably linked to a promoter which enables transcription of the DNA to produce the recombinant antigen for the vaccine.

The present invention further provides a method for vaccinating an equid against a *Sarcocystis neurona* infection comprising: (a) providing in a carrier solution a DNA in a plasmid which encodes at least one epitope of a 16 (±4) kDa antigen and/or 30 (±4) kDa antigen of *Sarcocystis neurona*; and (b) vaccinating the equid with the DNA in the carrier solution. Preferably, the DNA is in a carrier solution that is pharmaceutically accepted for DNA vaccines. In a preferred embodiment, the DNA is operably linked to a promoter to enable transcription of the DNA in a cell of the equid.

The present invention further provides a method for providing passive immunity to a *Sarcocystis neurona* infection in an equid comprising: (a) providing antibodies selected from the group consisting of polyclonal antibodies and monoclonal antibodies which are against at least one epitope of a 16 (±4) kDa antigen and/or 30 (±4) kDa antigen of *Sarcocystis neurona*; and (b) inoculating the equid. Preferably, the antibodies are provided in a pharmaceutically accepted carrier.

Further still, the present invention provides a method for producing an antigen comprising: (a) providing a microorganism in a culture containing a DNA encoding a fusion polypeptide comprising at least one epitope of a 16 (±4) kDa antigen and/or 30 (±4) kDa antigen of *Sarcocystis neurona* and a polypeptide that facilitates isolation of the fusion polypeptide; (b) culturing the microorganism in a culture to produce the fusion polypeptide; and (c) isolating the fusion polypeptide. In one embodiment, the fusion polypeptide is isolated by affinity chromatography which can be affinity chromatography that comprises an IgG-linked resin when the polypeptide consists of all or a portion of protein A, an $Ni^{2+}$ resin when the polypeptide is polyhistidine, amylose resin when the polypeptide is all or part of the maltose binding protein, or glutathione Sepharose 4B resin when the polypeptide is all or part of glutathione S-transferase.

Further still, the present invention provides a method for producing an antibody comprising: (a) providing a microorganism in a culture containing a DNA encoding a fusion polypeptide comprising at least one epitope of a 16 (±4) kDa antigen and/or 30 (±4) kDa antigen of *Sarcocystis neurona* linked to a polypeptide that facilitates isolation of the fusion polypeptide; (b) culturing the microorganisms in a culture to produce the fusion polypeptide; (c) isolating the fusion polypeptide; (d) producing the antibody from the polypeptide. In a preferred embodiment, the polypeptide is removed from the antigen position of the fusion polypeptide.

And further still, the present invention provides a method for producing a monoclonal antibody comprising: (a) providing a microorganism in a culture containing a DNA encoding a fusion polypeptide comprising at least one epitope of a 16 (±4) kDa antigen and/or 30 (±4) kDa antigen of *Sarcocystis neurona* linked to a polypeptide that facilitates isolation of the fusion polypeptide; (b) culturing the microorganism in a culture to produce the fusion polypeptide; (c) isolating the fusion polypeptide; and (d) producing the monoclonal antibody from the polypeptide. Preferably, the polypeptide is removed from the antigen portion of the fusion polypeptide.

The present invention comprises a vaccine for an equid comprising an isolated recombinant protein encoded by a cDNA produced from RNA of *Sarcocystis neurona* encoding a 16 (±4) kDa antigen and/or 30 (±4) kDa antigen, and a vaccine carrier. In another embodiment of the present invention, the vaccine for an equid comprise a recombinant virus vector containing DNA encoding a 16 (B±4) kDa antigen and/or 30 (±4) kDa antigen of *Sarcocystis neurona*, and a vaccine carrier. In particular, the recombinant virus is selected from the group consisting of equine herpesvirus, vaccinia virus, canary pox virus, raccoon poxvirus, adenovirus, and baculovirus. In an embodiment further still, the present invention comprises a DNA vaccine for an equid comprising a plasmid containing DNA encoding a 16 (±4) kDa antigen and/or 30 (±4) kDa antigen of *Sarcocystis neurona*.

The present invention provides a method for protecting an equid against *Sarcocystis neurona* which comprises providing a vaccine that when injected into the equid causes the equid to produce antibodies and cell mediated immunity against a 16 (±4) kDa antigen and/or 30 (±4) kDa antigen of the *Sarcocystis neurona* wherein the antibodies prevent infection by the *Sarcocystis neurona*. In particular, the vaccine comprises the 16 (±4) kDa antigen and/or 30 (±4) kDa antigen in a vaccine carrier. The present invention further provides a vaccine comprising a recombinant virus vector that expresses the 1 6 (±4) kDa antigen and/or 30 (±4) kDa antigen. In particular, the recombinant virus vector is selected from the group consisting of equine herpesvirus, vaccinia virus, canary pox virus, raccoon poxvirus, and adenovirus. The present invention further still provides a vaccine which comprises a DNA plasmid encoding the 16 (±4) kDa antigen and/or 30 (±4) kDa antigen.

The present invention further comprises a monoclonal antibody that selectively binds to a 16 (±4) kDa antigen and/or 30 (±4) kDa antigen of *Sarcocystis neurona*. The present invention also comprises an isolated recombinant protein encoded by a cDNA produced from RNA of *Sarcocystis neurona* encoding a protein which is a 16 (±4) kDa antigen and/or 30 (±4) kDa antigen. Thus, the present invention further comprises an isolated DNA that encodes a 16 (±4) kDa antigen and/or 30 (±4) kDa antigen of *Sarcocystis neurona*. Finally, the present invention comprises a bacterial clone containing a plasmid comprising a DNA encoding a 16 (±4) kDa antigen and/or 30 (±4) kDa antigen of *Sarcocystis neurona*. In particular, the bacterial clone expresses the 16 (±4) kDa antigen and/or 30 (±4) kDa antigen of *Sarcocystis neurona*.

It is therefore an object of the present invention to provide a vaccine for the prophylactic or therapeutic treatment of protozoal myeloencephalitis in equids. In particular, it is an object of the present invention to provide a vaccine for providing active immunity against *Sarcocystis neurona* which comprises a 16 (±4) kDa antigen and/or 30 (±4) kDa antigen of *Sarcocystis neurona*.

It is also an object of the present invention to provide a vaccine that provides passive immunity in an equid against *Sarcocystis neurona* which comprises antibodies against a 16 (±4) kDa antigen and/or 30 (±4) kDa antigen of *Sarcocystis neurona*.

These and other objects of the present invention will become increasingly apparent by reference to the following embodiments.

DESCRIPTION OF PREFERRED EMBODIMENTS

The following definitions are provided herein to promote a better understanding of the present invention.

The term "antibody" as used herein refers to an immunoglobulin molecule with the capacity to bind with a specific antigen as the result of a specific immune response. Immunoglobulins are serum proteins made up of light and heavy polypeptide chains and divisible into classes, which contain within them antibody activities toward a wide range of antigens.

The term "polyclonal antibody" as used herein refers to a mixed population of antibodies made against a particular pathogen or antigen. In general, the population contains a variety of antibody groups, each group directed towards a particular epitope of the pathogen or antigen. To make polyclonal antibodies, the whole pathogen or an isolated antigen is introduced by inoculation or infection into a host which induced the host to make antibodies against the pathogen or antigen.

The term "monoclonal antibody" as used herein refers to antibodies produced by a single line of hybridoma cells all directed towards one epitope on a particular antigen. The antigen used to make the monoclonal antibody can be provided as an isolated protein of the pathogen or the whole pathogen. A hybridoma is a clonal cell line that consists of hybrid cells formed by the fusion of a myeloma cell and a specific antibody-forming cell. In genera. monoclonal antibodies are of mouse origin; however, monoclonal antibody also refers to a clonal population of an antibody made against a particular epitope of an antigen produced by phage display technology or method that is equivalent to phage display or hybrid cells of non-mouse origin.

The term "antigen" as used herein refers to a substance which stimulates production of antibody or sensitized cells during an immune response. An antigen includes the whole pathogen or a particular protein of the pathogen. An antigen consists of multiple epitopes, each epitope of which is capable of causing the production of an antibody against the particular epitope.

The term "epitope" as used herein refers to an immunogenic region of an antigen which is recognized by a particular antibody molecule. In general, an antigen will possess one or more epitopes, each capable of binding an antibody that recognizes the particular epitope. An antibody can recognize a contiguous epitope which is an epitope that is a linear sequence of amino acids in the antigen molecule, or a non-contiguous epitope which is an epitope that spans non-contiguous amino acids in the antigen which have been brought together because of the three-dimensional structure of the antigen.

The term "active immunity" as used herein includes both antibody immunity and/or cell mediated immunity against *Sarcocystis neurona* induced by vaccinating an equid with the vaccine of the present invention comprising the 16 (±4) kDa antigen and/or 30 (±4) kDa antigen.

The term "passive immunity" as used herein refers to the protection against *Sarcocystis neurona* provided to an equid as a result of vaccinating the equid with a vaccine comprising antibodies against the 16 (±4) kDa antigen and/or 30 (±4) kDa antigen.

The present invention provides a vaccine that protects equids against *Sarcocystis neurona*. In a preferred embodiment, the vaccine consists of a 16 (±4) kDa antigen and/or 30 (±4) kDa antigen in a subunit vaccine. Preferably, the 16 (±4) kDa antigen and/or 30 (±4) kDa antigen are produced in a recombinant bacterium or eukaryote expression vector which produces the proteins which are then isolated to make the vaccine. In another embodiment of the vaccine, the vaccine is a DNA vaccine that comprises a recombinant DNA molecule, preferably in a plasmid, that comprises DNA encoding all or part of the 16 (±4) kDa antigen and/or 30 (±4) kDa antigen. In another embodiment of the vaccine, the recombinant DNA is inserted into a virus vector to provide a live vaccine which is a recombinant DNA virus. In U.S. Pat. No. 6,153,394 to Mansfield et al., which is hereby incorporated herein by reference, it was disclosed that *Sarcocystis neurona* possesses two unique antigens, a 16 (±4) antigen and a 30 (±4) kDa antigen. These antigens do not react with antibodies from other *Sarcocystis* spp. Thus, these antigens are useful for producing vaccines that protect equids against *Sarcocystis neurona*.

The route of administration for the vaccines of the present invention can include, but is not limited to, intramuscular, intraperitoneal, intradermal, subcutaneous, intravenous, intraarterial, intraocular, and oral as well as transdermal or by inhalation or suppository. The preferred routes of administration include intranasal, intramuscular, intraperitoneal, intradermal, and subcutaneous injection. The vaccine can be administered by means including, but not limited to, syringes, needle-less injection devices, or microprojectile bombardment gene guns (biolistic bombardment).

The vaccines of the present invention are formulated in pharmaceutically accepted carriers according to the mode of administration to be used. One skilled in the art can readily formulate a vaccine that comprises the polypeptide or DNA of the present invention. In cases where intramuscular injection is preferred, an isotonic formulation is preferred. Generally, additives for isotonicity can include sodium chloride, dextrose, mannitol, sorbitol, and lactose. In particular cases, isotonic solutions such as phosphate buffered saline are preferred. The formulations can further provide stabilizers such as gelatin and albumin. In some embodiments, a vasco-constriction agent is added to the formulation. The pharmaceutical preparations according to the present invention are provided sterile and pyrogen free. However, it is well known by those skilled in the art that the preferred formulations for the pharmaceutically accepted carrier which comprise the vaccines of the present invention are those pharmaceutical carriers approved in the regulations promulgated by the the United States Department of Agriculture, or equivalent government agency in a foreign country such as Canada or Mexico, for polypeptide, recombinant vector, antibody, and DNA vaccines intended for veterinary applications. Therefore, the pharmaceutically accepted carriers for commercial production of the vaccines of the present invention are those carriers that are already approved or will at some future date be approved by the appropriate government agency in the United States of America or foreign country.

Inoculation of an equid is preferably by a single vaccination which in the case of polypeptide, recombinant vector, and DNA vaccines produces a full, broad immunogenic response. In another embodiment of the present invention, the equid is subjected to a series of vaccinations to produce a full, broad immune response. When the vaccinations are provided in a series, the vaccinations can be provided between about 24 hours apart to two weeks or longer between vaccinations. In certain embodiments, the equid is vaccinated at different sites simultaneously.

The vaccines of the present invention are generally intended to be a prophylactic treatment which prevents *Sarcocystis neurona* from establishing an infection in an equid. However, the vaccines are also intended of the therapeutic treatment of equids already infected with *Sarcocystis neurona*. For example, antibody vaccines of the present invention are suitable for therapeutic purposes. However, vaccines that provide active immunity have also been shown to be effective when given as a therapeutic treatment against various diseases. Thus, the immunity that is provided by the present invention can be either active immunity or passive immunity and the intended use of the vaccine can be either prophylactic or therapeutic.

With respect to the above, the vaccine that elicits active immunity in a host can be a polypeptide vaccine or a DNA vaccine which produces the polypeptide in a vaccinated host. Alternatively, the vaccine can be a recombinant microorganism vaccine that expresses the 16 (±4) kDa antigen and/or 30 (±4) kDa antigen or a recombinant virus vector that expresses the 16 (±4) kDa antigen and/or 30 (±4) kDa antigen.

Thus, in one embodiment of the present invention, the active immunity is provided by a vaccine that consists of the isolated 16 (±4) kDa antigen and/or 30 (±4) kDa antigen or the 16 (±4) kDa antigen and/or 30 (±4) kDa antigen as a fusion polypeptide wherein the amino and/or carboxyl terminus is fused to another polypeptide, preferably a polypeptide that facilitates isolation of the fusion polypeptide. The fusion polypeptide comprising the vaccine is preferably produced in vitro in an expression system from a DNA that encodes the antigens which is in a microorganism such as bacteria, yeast, or fungi; in eukaryote cells such as a mammalian or an insect cell; or, in a virus expression vector such as adenovirus, poxvirus, herpesvirus, Simliki forest virus, baculovirus, bacteriophage, or sendai virus. In particular, suitable bacterial strains for producing the 16 (±4) kDa antigen and/or 30 (±4) kDa antigen or the 16 (±4) kDa antigen and/or 30 (±4) kDa antigen as fusion polypeptides include *Escherichia coli, Bacillus subtilis,* or any other bacterium that is capable of expressing heterologous polypeptides. Suitable yeast for expressing the 16 (±4) kDa antigen and/or 30 (±4) kDa antigen or 16 (±4) kDa antigen and/or 30 (±4) kDa antigen as fusion polypeptides include *Saccharomyces cerevisiae, Schizosaccharomyces pobme, Candida,* or any other yest capable of expressing heterologous polypeptides. Methods for using the aforementioned and the like to produce recombinant polypeptides for vaccines are well known in the art.

For any of the above, transformed host cells are cultured under conditions which produce the 16 (±4) kDa antigen and/or 30 (±4) kDa antigen or the 16 (±4) kDa antigen and/or 30 (±4) kDa antigen as fusion polypeptides. The resulting expressed polypeptides can be isolated from the culture, medium or cell extracts, using purification methods such as gel filtration, affinity chromatography, ion exchange chromatography, or centrifugation. Furthermore, the present invention further includes polypeptides that comprise only those epitopes of the 16 (±4) kDa antigen and/or 30 (±4) kDa antigen which are responsible for conferring protective immunity against *Sarcocystis neurona*. It is also understood that antigens of other *Sarcocystis* spp. that correspond to the 16 (±4) kDa antigen and/or 30 (±4) kDa antigen of *Sarcocystis neurona* are within the scope of the present invention.

DNA encoding the 16 (±4) kDa antigen and/or 30 (±4) kDa antigen can be obtained from a genome preparation of *Sarcocystis neurona* using a polymerase chain reaction (PCR) method that uses DNA primers which correspond to the nucleotide sequences encoding the amino and carboxyl ends of the 16 (±4) kDa antigen and/or 30 (35 4) kDa antigen. Preferably the 5' ends of the primers contain a restriction enzyme site that facilitates the subsequent steps of constructing 16 (±4) kDa antigen and/or 30 (±4) kDa antigen expression systems. Alternatively, the DNA primers can correspond to an internal region of the nucleotide sequence encoding the 16 (±4) kDa antigen and/or 30 (±4) kDa antigen for producing a DNA encoding a particular epitope of the antigen. Primer design and PCR methods are well known in the art.

In a preferred embodiment, the DNA is in a plasmid and the DNA is operably linked to a promoter which effects the expression of the 16 (±4) kDa antigen and/or 30 (35 4) kDa antigen in a microorganism, preferably *E. coli.* As used herein, the term "operably linked" means that the polynucleotide of the present invention and a DNA containing an expression control sequence, e.g., transcription promoter and termination sequences, are situated in a vector or cell such that expressing of the antigen encoded by the polynucleotide is regulated by the expression control sequence. Methods for cloning DNA such as the DNA encoding the 16 (±4) kDa antigen and/or 30 (±4) kDa antigen and operably linking DNA containing expression control sequences thereto are well known in the art. Expression of the 16 (±4) kDa antigen and/or 30 (±4) kDa antigen in a microorganism enables the antigen to be produced using fermentation technologies which are used commercially for producing large quantities of recombinant polypeptides.

To facilitate isolation of the 16 (±4) kDa antigen, and/or 30 (±4) kDa antigen produced as above, a fusion polypeptide is made wherein the antigen is linked to another polypeptide which enables isolation by affinity chromatography. Preferably, a fusion polypeptide is made using one of the aforementioned expression systems. Therefore, the DNA encoding the 16 (±4) kDa antigen and/or 30 (35 4) kDa antigen is linked to a DNA encoding a second polypeptide to produce a fusion polypeptide wherein the amino and/or carboxyl terminus of the antigen is fused to a polypeptide which allows for the simplified recovery of the antigen as a fusion polypeptide. The fusion of polypeptide can also prevent the antigen from being degraded during purification. While a vaccine comprising the fusion polypeptide is efficacious, in some instances it can be desirable to remove the second polypeptide after the purification. Therefore, it is also contemplated that the fusion polypeptide comprise a cleavage site at the junction between the antigen and the polypeptide. The cleavage site consists of an amino acid sequence that is cleaved with an enzyme specific for the amino acid sequence of that site. Examples of such cleavage sites that are contemplated include the enterokinase cleavage site which is cleaved by enterokinase, the factor Xa cleavage site which is cleaved by factor Xa, and the GENENASE cleavage site which is cleaved by GENENASE (GENENASE is a trademark of New England, Biolabs, Beverly, Mass.).

An example of a prokaryote expression system for producing the 16 (±4) kDa antigen and/or 30 (±4) kDa antigen is the Glutathione S-transferase (GST) Gene Fusion System available from Amersham Pharmacia Biotech, Piscataway, N.J., which uses the pGEX-4T-1 expression vector plasmid. The DNA encoding the antigen is fused in frame with the GST gene. The GST part of the fusion polypeptide allows the rapid purification of the fusion polypeptide using glutathione Sepharose 4B affinity chromatography. After purification, the GST portion of the fusion polypeptide can be removed by cleavage with a site-specific protease such as thrombin or factor Xa to produce a polypeptide free of the GST gene. The antigen free of GST is produced by a second round of glutathione Sepharose 4B affinity chromatography.

Another example for producing the 16 (±4) kDa antigen and/or 30 (±4) kDa antigen is a method which links in-frame with the gene encoding the antigen, codons that encode polyhistidine. The polyhistidine preferably comprises six histidine residues which allows purification of the fusion polypeptide by metal affinity chromatography, preferably nickel affinity chromatography. To produce the native antigen free of the polyhistidine, a cleavage site such as an enterokinase cleavage site is fused in frame between the codons encoding the polyhistidine and the codons encoding the antigen, The native polypeptide free of the polyhistidine is made by removing he polyhistidine by cleavage with enterokinase. The antigen free of the polyhistidine is produced by a second round of metal affinity chromatography. This method was shown to be useful for preparing the LcrV antigen of *Y. pestis* which was disclosed in Motin et al. *Infect. Immun.* 64: 4313-4318 (1996), which is hereby incorporated herein by reference. The Xpress System available from Invitrogen, Carlsbad, Calif. is an example of a commercial kit which is available for making and then isolating polyhistidine-polypeptide fusion proteins.

A method further still for producing the 16 (±4) kDa antigen and/or 30 (±4) kDa antigen is disclosed by Motin et al., *Infect. Immun.* 64: 3021-3029 (1995), which is hereby incorporated herein by reference. Motin et al. disclosed a DNA encoding a fusion polypeptide consisting of the DNA encoding an antigen linked to DNA encoding a portion of protein A wherein DNA encoding an enterokinase cleavage site is interposed between the DNA encoding protein A and the antigen. The protein A enables the fusion polypeptide to be isolated by IgG affinity chromatography, had the antigen free of the protein A is produced by cleavage with an enterokinase. The protein A is then remove by a second round of IgG affinity chromatography.

Another method for producing polypeptide vaccines against *Sarcocystis neurona* is based on methods disclosed in U.S. Pat. No. 5,725,863 to Daniels et al., which is hereby incorporated herein by reference. The Daniels method can be used to make the 16 (±4) kDa antigen and/or 30 (±4) kDa antigen vaccine of the present invention which consists of an enterotoxin which has inserted therein upwards of 100 amino acid residues of the 16 (±4) kDa antigen and/or 30 (±4) kDa antigen. Another method that can be used to make the polypeptide vaccines of the present invention is disclosed in U.S. Pat. No. 5,585,100 to Mond et al., which is hereby incorporated herein by reference, which provides methods for making various fusion polypeptide vaccines. Further methods are disclosed in U.S. Pat. No. 5,589,384 to Liscombe, which is hereby incorporated herein by reference. Finally, the pMAL Fusion and Purification System available from New England Biolabs is another example of a method for making a fusion polypeptide wherein a maltose binding protein is fused to the antigen. The maltose binding protein facilitates isolation of the fusion polypeptide by amylose affinity chromatography. The maltose binding protein can subsequently be released by cleavage with any of the aforementioned cleavage enzymes.

While bacterial methods are used to produce the 16 (±4) kDa antigen and/or 30 (±4) kDa antigen, it can be desirable to produce the antigen in a eukaryote expression system. A particularly useful system is the baculovirus expression system which is disclosed in U.S. Pat. No. 5,229,293 to Matsuura et al., which is hereby incorporated herein by reference. Baculovirus expression vectors suitable to produce the antigen are the pPbac and pMbac vectors from Stratagene; and the Bac-N-Blue vector, the pBlueBac4.5 vector, pBlueBacHis2-A,B,C, and the pMelBac available from Invitrogen, Carlsbad, Calif.

Another eukaryote system useful for expressing the 16 (±4) kDa antigen and/or 30 (±4) kDa antigen is a yeast expression system such as the ESP Yeast Protein Expression and Purification System available from Stratagene. Another yeast expression system is any one of the Pichia-based Expression systems from Invitrogen. Mammalian expression systems are also embraced by the present invention. Examples of mammalian expression systems are the LacSwitch II system, the pBK Phagemid, pXT1 vector system, and the pSG5 vector system from Stratagene; the pTargeT mammalian expression vector system, the pSI mammalian expression vector, pCI mammalian expression vector, and pAdVantage vectors available from Promega Corporation, Madison, Wis.; and the Ecdysone-Inducible Mammalian Expression System, pCDM8, pcDNA1.1, and pcDNA1.1/Amp available from Invitrogen.

Another method for producing the 16 (±4) kDa antigen and/or 30 (±4) kDa antigen in a eukaryote expression system is to insert DNA encoding the antigen into the genome of a eukaryote cell or in a eukaryote virus expression vector such as herpesvirus, poxvirus, or adenovirus to make a recombinant virus that expresses the antigen. The recombinant virus vectors are used to infect mammalian cells wherein the antigens are produced in the cell. U.S. Pat. No. 5,223,424 to Cochran et al., which is hereby incorporated herein by reference, provides methods for inserting genes into herpesvirus expression vectors. U.S. Pat. Nos. 5,338,683 and 5,494,807 to Paoletti et al. and U.S. Pat. No. 5,935,777 to Moyer et al., which are hereby incorporated herein by reference, provide methods for inserting genes into poxvirus expression vectors such as vaccinia virus, entomopoxvirus, and canary poxvirus. In another embodiment, the genes encoding the antigen can be inserted into a defective virus such as the herpesvirus amplicon vector which is disclosed in U.S. Pat. No. 5,928,913 to Efstathiou et al., which is hereby incorporated herein by reference. In any of the aforementioned virus vectors, the gene encoding the antigen are operably linked to a eukaryote promoter at the 5' end of the DNA encoding the protein and a eukaryote termination signal and poly(A) signal at the 3' end of the gene. Examples of such promoters are the cytomegalovirus immediate-early (CMV) promoter, the Rous sarcoma virus long terminal repeat (RSV-LTR) promoter, the simian virus 40 (SV40) immediate-early promoter, and inducible promoters such as the metallothionein promoter. An example of a DNA having a termination and poly(A) signal is the SV40 late poly(A) region. Another example of a viral expression system suitable for producing the antigen is the Sindbis Expression system available from Invitrogen. The use of these commercially available expression vectors and systems are well known in the art.

While subunit vaccines comprising the 16 (±4) kDa antigen and/or 30 (±4) kDa antigen generally provide good humoral protection, it can be desirable to provide the antigen as a component of a live recombinant vector vaccine. Therefore, the present invention further embraces recombinant virus vector vaccines wherein DNA encoding the antigen is inserted into a recombinant virus vector. In one embodiment of the recombinant virus vector vaccine, the DNA encoding the antigen is inserted into a herpesvirus vector according to the method taught by Cochran et al. in U.S. Pat. No. 5,233,424, which is hereby incorporated herein by reference. It is particularly desirable to have a recombinant virus vector vaccine against *Sarcocystis neurona* that is fetal safe, which allows the vaccine to be given to pregnant mares without affecting the fetus. U.S. Pat. Nos. 5,741,696 and 5,731,188 to Cochran et al., which are hereby incorporated herein by reference, teach methods for making and using live recombinant herpesvirus vaccine vectors which are fetal safe.

Other recombinant virus vector vaccines embraced by the present invention, include but are not limited to, adenovirus, adeno-associated virus, parvovirus, and various poxvirus vectors to express the 16 (±4) kDa antigen and/or 30 (±4) kDa antigen. For example, U.S. Pat. Nos. 5,338,683 and 5,494,807 to Paoletti et al. teach recombinant virus vaccines consisting of either vaccinia virus or canary poxvirus expressing foreign antigens; and U.S. Pat. No. 5,266,313 to Esposito et al. teaches recombinant raccoon poxvirus vectors expressing foreign antigens. Therefore, the present invention embraces recombinant poxvirus vaccines that express the 16 (±4) kDa antigen and/or 30 (±4) kDa antigen made according to the methods taught in any one of U.S. Pat. Nos. 5,338,683; 5,494,807; and 5,935,777, which are hereby incorporated herein by reference.

While the above refer to DNA sequences encoding the 16 (±4) kDa antigen and/or 30 (±4) kDa antigen, the present invention also includes RNA sequences for encoding the antigen.

The present invention further includes vaccines that comprise the 16 (±4) kDa antigen and/or 30 (±4) kDa antigen or particular epitopes of the 16 (±4) kDa antigen and/or 30 (±4) kDa antigen as components of a heat-stable spore delivery system made according to the method taught in U.S. Pat. No. 5,800,821 to Acheson et al., which is hereby incorporated herein by reference. Therefore, the present invention provides a generically engineered bacterial cell containing DNA encoding the 16 (±4) kDa antigen and/or 30 (±4) kDa antigen. When the recombinant bacterial spore vaccine is orally administered to the equid, the spores germinate in the gastrointestinal tract of the animal and the bacteria expresses the antigen which comes into contact with the animal's immune system and elicits an immune response. The vaccine has the advantage of being heat stable; therefore, it can be stored at room temperature for an indefinite period of time.

Another embodiment of the *Sarcocystis neurona* vaccine is a DNA vaccine that elicits an active immune response in an equid. The DNA vaccine consists of DNA having a DNA sequence substantially similar to the DNA sequence that encodes the 16 (±4) kDa antigen and/or 30 (±4) kDa antigen. The DNA encoding the antigen is operably linked at or near its start codon to a promoter that enables transcription of the antigen from the DNA when the DNA is the cells of the equid. Preferably, the DNA is in a plasmid. Promoters for expression of DNAs in DNA vaccines are well known in the art and include among others such promoters as the RSV LTR promoter, the CMV immediate early promoter, and the SV40 T antigen promoter. It is further preferred that the DNA is operably linked at the or near the termination codon of the sequence encoding antigen to a DNA fragment comprising a transcription termination signal and poly(A) recognition signal. Preferably, the vaccine is in an accepted pharmaceutical carrier or in a lipid or liposome carrier similar to those disclosed in U.S. Pat. No. 5,703,055 to Felgner, which is hereby incorporated herein by reference. The DNA can be provided to the equid by a variety of methods such as intramuscular injection, intrajet injection, or biolistic bombardment. Making DNA vaccines and methods for their use are provided in U.S. Pat. Nos. 5,589,466 and 5,580,859, both to Felgner, which are hereby incorporated herein by reference. Finally, a method for producing pharmaceutical grade plasmid DNA is taught in U.S. Pat. No. 5,561,064 to Marquet et al., which is hereby incorporated herein by reference.

Therefore, using the abovementioned methods, DNA vaccines that express the 16 (±4) kDa antigen and/or 30 (±4) kDa antigen are made and used to vaccinate equids against *Sarcocystis neurona*. The advantage of the DNA vaccine is that the DNA is conveniently propagated as a plasmid which is a simple and inexpensive means for producing a vaccine, and since the vaccine is not live, the regulatory difficulties associated with getting recombinant virus vaccines approved are not present. One skilled in the art would appreciate that while the polypeptide produced for the polypeptide vaccine or by the DNA vaccine can be the entire 16 (±4) kDa antigen and/or 30 (±4) kDa antigen, the present invention also includes polypeptide and DNA vaccines wherein the vaccine consists of a subfragment of the antigen which comprises one or more epitopes of the antigen or a DNA encoding one or more epitopes of the antigen. Furthermore, the polypeptide and DNA vaccines of the present invention can comprise synthetically produced polypeptides or DNA which are made by chemical synthesis methods well known in the art.

While the DNA and polypeptide provided herein is from *Sarcocystis neurona*, the present invention further encompasses similar antigens from other *Sarcocystis* spp. Thus, it is anticipated that the vaccines and methods disclosed herein are useful for producing vaccines against other *Sarcocystis* spp.

In another embodiment of the present invention, the vaccine provides passive immunity to *Sarcocystis neurona*. A vaccine that elicits passive immunity against *Sarcocystis neurona* consists of polyclonal antibodies or monoclonal antibodies that are against the unique 16 (±4) and/or 30 (±4) antigen of *Sarcocystis neurona*.

To make a passive immunity vaccine comprising polyclonal antibodies, the 16 (±4) kDa antigen and/or 30 (±4) kDa antigen or one or more epitopes therefrom are injected into a suitable host for preparing the antibodies, preferably the host is a horse, swine, rabbit, sheep, or goat. Methods for producing polyclonal antibody vaccines form these hosts are well known in the art. By way of brief example, the antigen is admixed with an adjuvant such as Freund's complete or the less toxic TiterMax available from CytRx Corp., Norcross, Ga., which then administered to the host by methods well known in the art.

The passive immunity vaccine can comprise one or more monoclonal antibodies against one or more epitopes of the 16 (±4) kDa antigen and/or 30 (±4) kDa antigen. Methods and hybridoma for producing monoclonal antibodies are well known in the art. While monoclonal antibodies can be made using hybridoma technologies well known in the art, the monoclonal antibodies against the antigen can also be made according to phage display methods such as that disclosed in U.S. Pat. No. 5,977,322 to Marks et al., which is hereby incorporated herein by reference. Equinized antibodies against the antigen can be made according to methods which have been used for humanizing antibodies such as those disclosed in U.S. Pat. Nos. 5,693,762 and 5,693,761 both to Queen et al., which are hereby incorporated herein by reference. A phage display kit that is useful for making monoclonal antibodies is the Recombinant Phage Antibody System available form Amersham Pharmacia Biotech.

To make the vaccines of the present invention, the genes encoding the 16 (±4) kDa antigen and/or 30 (±4) kDa antigen are identified using monoclonal antibodies against the 16 (±4) kDa antigen and/or 30 (±4) kDa antigen to screen a cDNA expression library made from mRNA isolated from *Sarcocystis neurona*. Since expression of certain *Sarcocystis neurona* proteins is stage specific, not only are cDNA expression libraries made from mRNA isolated from *Sarcocystis neurona* grown in culture but cDNA libraries are also made from mRNA isolated from *Sarcocystis neurona* at various stages of development, i.e., the merozoite, sporocyst, and sarcocyst stages. Methods for screening cDNA expression libraries with monoclonal antibodies are described in *Molecular Cloning: A Laboratory Manual, Second Edition*, edited by Sambrook et al. Cold Spring Harbor Laboratory Press, Cold Spring Harbor, N.Y. (1989). The expression library can be a plasmid-based expression library that uses a pUC, pUR, pEX or a lambda-based expression library. Preferably, the library is a ZAP EXPRESS vector (available from Stratagene, La Jolla, Calif.) which is a hybrid lambda-plasmid vector used to construct cDNA libraries. RNA is isolated using a Stratagene RNA isolation kit and cDNA is made using the ZAP EXPRESS cDNA Synthesis kit (available from Stratagene). The library is screened using monoclonal antibodies against the 16 (±4) kDa antigen and/or 30 (±4) kDa antigen and the picoBLUE Immunoscreening kit (available from Stratagene).

An important aspect of any vaccination program is to be able to distinguish animals vaccinated against a disease from animals infected with the disease. Therefore, the present invention further includes methods that distinguish equids vaccinated with the vaccine of the present invention from equids infected with *Sarcocystis neurona*, or equids vaccinated with whole-organism *Sarcocystis neurona* vaccine preparations, or equids never exposed to *sarcocystis neurona*. In one embodiment, to distinguish vaccinated equids from infected equids, a biological sample from an equid is tested for the presence of antibodies against *Sarcocystis neurona* specific antigens that are in addition to the 16 (±4) antigen and 30 (±4) kDa antigen which are induced by the vaccine. For example, Granstrom et al. in J. Vet. Diagn. Invest. 5: 88-90 (1993) identified by gel electrophoresis followed by Western blot eight *Sarcocystis neurona* antigens; 70 kDa, 24 kDa, 23.5 kDa, 22.5 kDa, 13 kDa, 11 kDa, 10.5 kDa, and 10 kDa, of which at least three (22.5 kDa, 13 kDa, and 10.5 kDa) were common to all seven equids infected with *Sarcocystis neurona*. Therefore, an equid that had antibodies against any of the above *Sarcocystis neurona* antigens in addition to the 16 (±4) and 30 (±4) kDa antigens would be infected with, or exposed to, *Sarcocystis neurona* whereas an equid that had antibodies against the 16 (±4) antigen and 30 (±4) kDa antigen but not against any one of the other *Sarcocystis neurona* antigens would be an equid that had been vaccinated with the vaccine of the present invention but was not infected with *Sarcocystis neurona*.

Therefore, in a Western blot embodiment consisting of *Sarcocystis neurona* antigens resolved by gel electrophoresis, a biological sample from a vaccinated equid would contain antibodies that bind only with the 16 (±4) antigen and 30 (±4) kDa antigen whereas a sample from an equid infected with, or exposed to, *Sarcocystis neurona* would contain antibodies that bind with additional *Sarcocystis neurona* antigens. The equine antibodies that are bound are identified by treating the blot with labeled antibodies against equine antibodies. Preferably, the label is selected from the group consisting of alkaline phosphatase, horseradish peroxidase, fluorescent compounds, luminescent compounds, colloidal gold, and magnetic particles. Methods for preparing and analyzing Western blots are well known in the art. In a preferred embodiment, the Western blot is pretreated with non-equine antibodies against a *Sarcocystis* sp. other than *Sarcocystis neurona* wherein the pretreatment prevents binding of equine antibodies to those antigens common to all *Sarcocystis* spp. which can be present in the sample. This method is disclosed in U.S. Ser. No. 09/506,630, filed Feb. 18, 2000, which is hereby incorporated herein by reference.

In an enzyme-linked immunosorbent assay (ELISA) embodiment, a microtiter plate is provided containing a plurality of wells wherein a first well or series of wells contains the 16 (±4) kDa antigen immobilized to the surface therein, a second well or series of wells contains the 30 (±4) kDa antigen immobilized to the surface therein, and a third well or series of wells contains another *Sarcocystis neurona* specific antigen immobilized to the surface therein. Next, the biological sample is added to the wells containing the bound antigens and antibodies against *Sarcocystis neurona* are allowed to bind to form an antibody-antigen complex. The biological sample can be provided neat or in a limiting dilution series in a physiological solution. Unbound material in the sample is removed from the antibody-antigen complex by washing. The complex is then reacted with a labeled antibody or labeled monoclonal antibody that binds to equine antibodies to form a second antibody-antigen complex. The second complex can be detected when the labeled monoclonal or polyclonal antibody is conjugated to a reporter ligand such as horseradish-peroxidase or alkaline phosphatase. Alternatively, the second monoclonal or polyclonal antibody can be conjugated to reporter ligands such as a fluorescing ligand, biotin, colored latex, colloidal gold magnetic beads, radioisotopes or the like. Detection of the complex is by methods well known in the art for detecting the particular reporter ligand. Therefore, a sample from an equid that had been vaccinated will produce antibodies against only the 16 (±4) antigen and 30 (±4) kDa antigen whereas a sample from an equid that is infected with, or exposed to, *Sarcocystis neurona* will contain antibodies against the third antigen in addition to containing antibodies against the 16 (±4) antigen and 30 (±4) kDa antigen. ELISA was developed by Engvall et al., *Immunochem.* 8: 871 (1971) and further refined by others such as Ljunggren et al. *J. Immunol. Meth.* 104: 7-14 (1987) and Kemeny et al., *J. Immunol. Meth.* 87: 45-50 (1986). ELISA and its variations are well known in the art. The ELISA can be provided as a kit for distinguishing vaccinated equid from unvaccinated equid, and from an equine infected with *Sarcocystis neurona*.

Since it is important to be able to test samples in the field in order to distinguish equids infected with *Sarcocystis neurona* from equids vaccinated with the vaccine of the present invention, the present invention further includes rapid immunodiffusion-based methods, their devices, and kits comprising the same. Therefore, the present invention can be provided with a kit that comprises any one of the methods described in U.S. Pat. No. 5,620,845 to Gould et al., U.S. Pat. No. 5,559,041 to Kang et al., U.S. Pat. No. 5,656,448 to Kang et al., U.S. Pat. No. 5,728,587 to Kang et al., U.S. Pat. No. 5,695,928 to Stewart et al., U.S. Pat. No. 5,169,789 to Bernstein et al. U.S. Pat. No. 4,486,530 to David et al., and U.S. Pat. No. 4,786,589 to Rounds et al. While the aforementioned disclose particular rapid immunodiffusion methods, the present invention is not to be construed to be limited to the aforementioned. It is within the scope of the present invention to embrace derivations and modifications of the aforementioned. For example, the 16 (±4) antigen and/or 30 (±4) kDa antigen are immobilized to one area of a membrane and a third *Sarcocystis neurona* antigen is immobilized to another area of the membrane in a device designed for analyzing a biological sample. A biological sample is applied to the membrane which diffuses throughout the membrane. If the sample contains antibodies that form antibody-antigen complexes with all three antigens, the equid is infected with, or exposed to, *Sarcocystis neurona*. If the sample contains antibodies that form complexes with the 16 (±4) and/or 30 (±4) kDa antigens and no antibodies that bind to the third antigen, the equid has been vaccinated with the vaccine of the present invention but is not infected with *Sarcocystis neurona*. Detection of the antibody-antigen complex is by a colorimetric method incorporated into the device, by immersing the device into a solution that causes a colorimetric reaction, or by reacting with a labeled monoclonal or polyclonal antibody conjugated to a reporter ligand.

Another method for distinguishing vaccinated equids from equids infected with, or exposed to *Sarcocystis neurona* is to provide as the vaccine the aforementioned fusion polypeptide wherein the polypeptide comprises a marker epitope that elicits an antibody in the vaccinated equid that would not normally be present in the equid. For example, the marker epitope could be from a pathogen that does not infect equids or a synthetic polypeptide that elicits an antibody in equids that would not normally occur in equids. Therefore, if a sample from an equid contained antibodies against the marker epitope and the 16 (±4) antigen and/or 30 (±4) kDa antigen, the equid was vaccinated with the vaccine of the present invention, whereas if the sample does not contain antibodies against the marker epitope but does contain antibodies against the 16 (±4) antigen and/or 30 (±4) kDa antigen, the equid is injected with *Sarcocystis neurona*. The sample is tested according to any of the aforementioned diagnostic methods.

In a method further still for distinguishing vaccinated equids from infected equids, the vaccine of the present invention consists of a polypeptide that comprises a subset of the total epitopes on the 16 (±4) antigen and or 30 (±4) kDa antigen. Therefore, in an equid vaccinated with the above polypeptide vaccine, antibodies are produced against only those epitopes on the polypeptide whereas in an equid infected with *Sarcocystis neurona*, antibodies are produced against all of the epitopes. Thus, a sample from an infected equid will produce antibodies that binds the vaccine polypeptide and the full-sized antigen whereas a sample from a vaccinated equid will produce antibodies that will bind the vaccine polypeptide but not the full-sized antigen. The antibody-antigen or antibody-polypeptide complex can be detected by modifying any of the aforementioned diagnostic assays.

The following examples are intended to promote a further understanding of the present invention.

EXAMPLE 1

This example is to demonstrate the preparation of monoclonal antibodies that recognize 16 (±4) kDa antigen and/or 30 (±4) kDa antigen of *Sarcocystis neurona*.

*Sarcocystis neurona* was cultured on equine dermal cell line cultures as taught in Example 3 or on bovine monocyte cell cultures as taught by Granstrom et al., *J. Vet. Diagn. Invest.* 5: 88-90 (1993). *Sarcocystis neurona* merozoites were harvested and the 16 (±4) kDa antigen and/or 30 (±4) kDa antigen were purified by methods known to the art for purifying antigens, i.e., the 16 (±4) kDa antigen and/or 30 (±4) kDa antigen were purified from merozoites by two-dimensional polyacrylamide gel electrophoresis. Then the purified antigens are used to make monoclonal antibodies according to the methods in *Antibodies, A Laboratory Manual*, eds. Harlow and Lane, Cold Spring Harbor Laboratory Press, Cold Spring Harbor, N.Y. (1988), well known to those skilled in the art as a source for methods for making polyclonal and monoclonal antibodies.

BALB/c mice are immunized with an initial injection of 1.0 μg of the 16 (±4) kDa antigen and/or 30 (±4) kDa antigen per mouse mixed 1:1 with Freund's complete adjuvant. After two weeks, a booster injection of 1.0 μg of antigen is injected into each mouse intravenously without adjuvant. Three days after the booster injection the mouse serum is checked for antibodies to the 16 ±4 kDa and/or 30 ±4 kDa antigens. If positive, a fusion is performed with a mouse myeloma cell line. Mid log phase myeloma cells are harvested on the day of fusion, checked for viability, and separated from the culture medium by low-speed centrifugation. Then the cells are resuspended in serum-free Dulbecco's Modified Eagle's medium (DMEM).

The spleens are removed from the immunized mice and washed three times with serum-free DMEM and placed in a sterile Petri dish containing 20 ml of DMEM containing 20% fetal bovine serum, 1 mM pyruvate, 0.100 units penicillin, and 100 units streptomycin. The cells are released by perfusion with a 23 gauge needle. Afterwards, the cells are pelleted by low-speed centrifugation and the cell pellet is resuspended in 5 ml 0.17 M ammonium chloride and placed on ice for several minutes. Then 5 ml of 20% bovine fetal serum is added and the cells pelleted by low-speed centrifugation. Afterwards, the cells are resuspended in 10 ml DMEM and mixed with myeloma cells to give a ratio of 3:1. The cell mixture is pelleted by low-speed centrifugation, the supernatant fraction removed, and the pellet allowed to stand for 5 minutes. Next, over a period of 1 minute, 1 ml of 50% polyethylene glycol (PEG) in 0.01 M HEPES pH 8.1 at 37° C. is added. After 1 minute incubation at 37° C., 1 ml of DMEN is added for a period of another 1 minute, then a third addition of DMEM is added for a further period of 1 minute. Finally, 10 ml of DMEM is added over a period of 2 minutes. Afterwards, the cells are pelleted by low-speed centrifugation and the pellet resuspended in DMEM containing 20% fetal bovine serum, 0.016 mM thymidine, 0.1 hypoxanthine, 0.5 µM aminopterin, and 10% hybridoma cloning factor (HAT medium). The cells are then placed into 96-well plates.

After 3, 5, and 7 days half the medium in the plates is removed and replaced with fresh HAT medium. After 11 days, the hybridoma cell supernatant is screened by an ELISA assay. In this assay, 96-well plates are coated with the appropriate 16 (±4) kDa antigen or 30 (±4) kDa antigen. One hundred µl of supernatant from each well is added to a corresponding well on a screening plate and incubated for 1 hour at room temperature. After incubation, each well is washed three times with water and 100 µl of a horseradish peroxide conjugate of goat anti-mouse IgG (H+L), A, M (1:1,500 dilution) is added to each well and incubated for 1 hour at room temperature. Afterwards, the wells are washed three times with water and the substrate OPD/hydrogen peroxide is added and the reaction is allowed to proceed for about 15 minutes at room temperature. Then 100 µl of 1 M HCl is added to stop the reaction and the absorbance of the wells is measured at 490 nm. Cultures that have an absorbance greater than the control wells are removed to 2 cm$^2$ culture dishes, with the addition of normal mouse spleen cells in HAT medium. After a further three days, the cultures are rescreened as above and those that are positive are cloned by limiting dilution. The cells in each 2 cm$^2$ culture are counted and the cell concentration adjusted to 1×10$^5$ cells per ml. The cells are diluted in complete medium and normal mouse spleen cells are added. The cells are plated in 96-well plates for each dilution. After 10 days, the cells are screened for growth. The growth positive wells are screened for antibody production; those testing positive are expanded to 2 cm$^2$ cultures and provided with normal mouse spleen cells. This cloning procedure is repeated until stable antibody producing hybridomas are obtained. Then the identified stable hybridomas are progressively expanded to larger culture dishes to provide stocks of the cells.

Production of acities fluid is performed by injecting intraperitoneally 0.5 ml of pristane into female mice to prime the mice for ascites production. After 10 to 60 days, 4.5×10$^6$ cells are injected intraperitoneally into each mouse and ascities fluid is harvested between 7 and 14 days later.

An alternate method for screening hybridomas for antibody production is as follows. *Sarcocystis neurona* is heat-denatured in 0.5 M Tris (pH 7.4) with 10% SDS, 20% glycerol and 5% 2-mercaptoethanol. The denatured antigens are separated by SDS-polyacrylamide gel electrophoresis in a 12-20% (v/v) linear gradient gel with a 4% (v/v) stacking gel. The separated antigens are electrophoretically transferred to Western PVDF membranes at 100 volts for 1.5 hours, then 150 volts for 0.5 hours. The membranes are then blocked overnight in 1% by volume bovine serum albumen in 0.5% Tween-Tris buffered saline (Blocking buffer). The blots are air-dried and stored frozen. Prior to use, the membranes are incubated with bovine serum albumin and *Sarcocystis cruzi* antibodies in Blocking buffer at a range of 1:10 to 1:100 ratio for two hours. Afterwards, the membranes are washed in 0.5% Tween-Tris buffered saline and then incubated with monoclonal antibodies from the various hybridoma clones. The membranes are developed as disclosed in the prior art, e.g., Granstrom et al., J. Vet. Diag. Invest. 5: 88-90 (1993) or *Antibodies, A Laboratory Manual*, eds. Harlow and Lane, Cold Spring Harbor Laboratory Press, Cold Spring Harbor, N.Y. (1988).

Hybridomas that successfully produce monoclonal antibodies against various epitopes of the 16 (±4) kDa antigen and 30 (±4) kDa antigen are expanded as above, and used to make monoclonal antibodies for the antigen-based immunoassay and for identifying cDNA library clones in Example 2 that contain *Sarcocystis neurona* DNA which express either the 16 (±4) and/or 30 (±4) kDa antigens.

In the foregoing procedure, monoclonal antibodies against particular epitopes of the identifying antigens are produced.

EXAMPLE 2

This example shows the preparation of a cDNA library that expresses the 16 (±4) kDa antigen and/or 30 (±4) kDa antigen or *Sarcocystis neurona*. The methods for making and screening cDNA expression libraries are well known to those skilled in the art and are described in *Molecular Cloning: A Laboratory Manual, Second Edition*, edited by Sambrook et al. Cold Spring Harbor Laboratory Press, Cold Spring Harbor, N.Y. (1989). The monoclonal antibodies made as in Example 1 are used to screen the library for clones that express the 16 (±4) kDa antigen and/or 30 (±4) kDa antigen.

EXAMPLE 3

This example provides a simplified method for the isolation, excystation, and culture of *Sarcocystis* species using opossums as a model. The method is an improvement over the isolation, excystation and culture methods of the prior art and is useful for producing antigens from various *Sarcocystis neurona* strains for subunit vaccines, for making monoclonal and polyclonal antibody vaccines, and attenuated and killed whole organism vaccines.

Opossums are humanely killed and their intestines screened for *Sarcocystis* spp. oocysts. In addition, *Sarcocystis* oocysts collected from wild grackle (*Quiscalus* sp.) fed possums and oocysts collected from wild-caught cowbird (*Molothrus ater*) fed opossums in the inventors' laboratory can be used. A 2-cm segment of mid-small intestine from each animal is removed and washed with 0.01 M phosphate-buffered saline, pH 7.4 (PBS). A scraping of mucosa is observed at 100× magnification using a Nikon Optiphot-2 microscope to determine the presence or absence of oocysts. Feces from the large intestine is removed from each positive animal and tested for the presence of *Sarcocystis* spp. sporocysts and other parasite ova by sucrose flotation according to Sloss et al., In *Veterinary Clinical Parasitology*, Iowa State University Press, Ames, Iowa, (1994), p. 198. The small intestine is flushed with PBS to remove contents and slit lengthwise. The mucosa is scraped off with a glass slide and ground in a Dounce homogenizer. The slurry is transferred to a conical tube and washed three times with PBS by centrifugation for 10 minutes at 500×g. The pellet is resuspended in 3 volumes of pepsin-NaCl-HCl (0.65% pepsin w/v, 0.86% NaCl w/v, 1% concentrated HCl v/v) and incubated at 37° C. for 1.5 hours with frequency mixing. The slurry is washed 3 times with PBS as above and the pellet stored in Hank's balanced salt solution (HBSS) plus penicillin (100 units/ml), amikacin (100 µg/ml), and amphotericin B (1.25 µg/ml) until further use. A 1 to 3 ml aliquot of the semidigested mucosa is concentrated by centrifugation for 10 minutes at 500×g. The pellet is suspended in 15 ml of 2.6% sodium hypochlorite solution, stirred for 1.5 hours at room temperature, and washed once with PBS as above.

The improvement in the excystation and culture of *Sarcocystis* sp. over the prior art is the mechanical excystation step as set forth below. The washed sodium hypochlorite pellet is suspended in 15 ml 10% trypsin in alkaline chelating solution (ACS) which is a solution that consisted of 100 mM NaCl, 3 mM KCl, 9 mM $Na_2HPO_4$, 3 mM Na-citrate, 0.5 mM $Na_2EDTA$, 0.1% glucose, 0.3% HEPES, 100 units penicillin, and 1.25 μg/ml amphotericin B, and incubated 1.5 hour at 37° C. After washing once with PBS as above, a drop of the pellet is compressed between sterile slides and shearing forces are applied by moving the slides back and forth. The material of the slides is washed with cell medium into flasks of confluent equine dermal cells (ATCC CCL-57, freely available from the America Type Culture Collection, 10801 University Boulevard, Manassas, Va. 20110-2209) in Dulbecco's modified Eagle's medium (DMEM; available from GIBCO a division of Life Technologies, Bethesda, Md.) plus L-glutamine, 6% heat-inactivated fetal bovine serum, penicillin (100 units/ml), amikacin (100 μg/ml), and amphotericin B (1.25 μg/ml). *Sarcocystis neurona* isolated from neural tissue of EPM-affected horses can be passaged continuously long term on this cell line. Before and after inoculation, equine dermal cells are grown at 37° C. with 5% $CO_2$, with medium changed every other day for 7 days and weekly thereafter. After inoculation, cultures are observed weekly for evidence of cellular damage due to *Sarcocystis* spp. replication and for the presence of extracellular merozoites using an Olympus CK2 inverted microscope. Positive cultures are confirmed by Romanowsky (modified Giemsa-Wright)-stained cytospin of infected cells using a Shandon Cytospin 3 centrifuge and a Wescor 7100 Aerospray slide stainer. Separate sterile pipettes are used to add or withdraw media from each flask containing each separate strain to eliminate the possibility of cross contamination.

The above improved method enabled obtaining viable organisms from 7 opossums that had *Sarcocystis* sporocysts detected in the feces. All of these opossums were adult males, 6 of which were from the same Michigan farm on which two horses had been diagnosed with histopathologically confirmed EPM. Each opossum harbored a million or more oocysts in the small intestinal mucosa; however, fewer than two sporocysts per gram of feces were observed in each when feces from the large intestine was tested by sucrose flotation. Ascarid, strongyle, tapeworm, *Caillaria* sp., *Physaloptera* sp. eggs, or a combination of these eggs were also observed in the wild-caught animals.

In the improved method, processing the mucosa with a Dounce homogenizer and subsequent pepsin-NaCl-HCl digestion broke down tissues but did not disrupt *Sarcocystis* oocysts, man of which were still attached to tissue fragments (Murphy and Mansfield, 1999). Further digestion with sodium hypochlorite freed most of the oocysts and released many sporocysts. Three chemical excystation methods as set forth in Example 4 were attempted. All were effective in breaking down the oocyst walls and weakening the sporocyst walls, but none to few excysted sporocysts were detected afterward. However, mechanical excystation as performed according to the improvement shown herein proved to be most effective, especially with the 10% trypsin ACS pretreated sporocysts.

Processed small intestine from the first opossum isolate refrigerated in HBSS plus penicillin, streptomycin, and amphotericin B remained contaminated with bacteria. Inoculation of dermal cells with this contaminated material resulted in cell death. Culture and sensitivity testing proved the contaminating organism to be *Alcalcigens* sp. Amikacin (100 μg/ml) was substituted for the streptomycin in the mucosal preparation and in all subsequent solutions, including the cell growth media. Amikacin killed the contaminant and no bacterial contamination of any subsequent isolates using the penicillin-amikacin-amphotericin B-enhanced media.

Successful culture of merozoites from the first opossum isolate occurred in 13 of 15 flasks into which sporocysts pretreated with 10% trypsin in ACS and mechanically excysted by the improved method herein were inoculated. In contrast, 4 flasks each were inoculated with the three different regimes of chemically excysted sporocysts without mechanical excystation as shown in Comparative Example 1. All remained negative except for 1 trypsin-ACS- and 1 bile-trypsin-pretreated inoculum.

Thus, the trypsin-ACS/mechanically excysted sporocysts made as above, infected more efficiently than those prepared by chemical methods; each flask became positive by visual examination at about 10 to 30 sites between about 5 to 15 days after inoculation. In contrast, the trypsin-ACS pretreated sporocysts became positive in culture 14 days after inoculation and at one site, and the bile-trypsin-pretreated sporocysts became positive in culture 26 days after inoculation at only one site. Successful culture was further confirmed by Romanowsky-stained cytospin of infected cells. All flasks negative for merozoites visually and by Romanowsky-stained cytospin of cells were discarded eight weeks after inoculation because longer term culture did not result in more positive flasks in preliminary trials. The mechanical excystation method has been used for all subsequent opossum isolates. The six additional isolates became positive using microscope visualization from 6 to 14 days after inoculation at many sites in each flask. All strains isolated from these seven opossums have grown well long term (six months or longer).

Sporocysts collected from six specific pathogen-free opossums fed wild-caught cowbird were successfully excysted and grown in equine dermal cell culture in our laboratory using this technique as were sporocysts thought to be *Sarcocystis falcatula* from opossums fed wild-caught grackle (these were wild-caught opossums testing negative for *Sarcocystis* by fecal flotation for three weeks prior to infection). The cowbird isolates have grown well long term in equine dermal cells. Marsh et al., J. Parasitology 83: 1189-1192 (1997) have shown that an equine-derived *Sarcocystis neurona* isolate grew highly efficiently long term in equine dermal cells. The grackle-fed opossum isolate grew in equine dermal cells but only for a brief time, 3 to 8 weeks in three different infection trials. Although the cell line was not effective for long-term growth of this *Sarcocystis* sp., the excystation method and initial culture were successful.

This example shows that multiple isolates of merozoites have been successfully cultured from opossum-derived *Sarcocystis* spp. oocysts using the improved method of digestion followed by manual excystation. Long-term growth of all opossum *Sarcocystis* spp. should be possible using the improvement and the appropriate cell line. Equine dermal cells work well for *Sarcocystis neurona*, but other cell lines may be more useful for other *Sarcocystis* spp. A more complete understanding of the life cycle of *Sarcocystis neurona* and, therefore, of the factors that determine exposure of horses should be possible using the opossum isolates derived from the above improved excystation and culture methods.

EXAMPLE 4

This example provides three chemical excystation methods for preparing *Sarcocystis* sp. oocysts. The chemically prepared samples were compared to samples prepared by the improved method shown in Example 3.

Samples were prepared as in Example 3 except that after washing the pellet that had been suspended in 2.6% sodium hypochlorite, the samples were treated with either (1) 10% trypsin in ACS, (2) 10% bile and 2% trypsin in HBSS (Speer et al., J. Protozoology 33: 486-490 (1986)), or 5% sodium taurocholate and 2% trypsin in PBS (Speer et al., ibid.). All the samples were incubated at 37° C. and 5% $CO_2$. The chemical methods provided poor results even though the methods were effective in breaking down the oocyst walls and weakening the sporocyst walls.

Flasks inoculated with samples from the three above chemically excysted sporocysts remained negative except for one trypsin-ACS- and one bile-trypsin-pretreated inoculum. The trypsin-ACS-pretreated sporocysts became positive in culture 14 days after inoculation in one site and the bilt-trypsin-pretreated sporocysts became positive in culture 26 days after inoculation at one site. In contrast, the improved method as was shown in Example 3 was more efficient. Each flask became positive by visual examination at many sites 5 to 15 days post-inoculation.

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the Claims attached herein.

We claim:

1. A method for treating an equid infected with *Sarcocystis neurona* comprising:
   (a) providing a mixture of antibodies against a 16 ±4 kDa antigen and a 30 ±4 kDa antigen, both of which are specific to *Sarcocystis neurona*, wherein the antibodies are selected from the group consisting of polyclonal antibodies from serum from an animal immunized with the antigen and monoclonal antibodies from a hybridoma, and wherein the antibodies are in a pharmaceutically acceptable carrier; and
   (b) inoculating the equid with the antibodies in the carrier to treat the equid.

2. The method composition of claim 1 wherein the antibodies are monoclonal antibodies.

\* \* \* \* \*

UNITED STATES PATENT AND TRADEMARK OFFICE
CERTIFICATE OF CORRECTION

PATENT NO. : 7,510,720 B1
APPLICATION NO. : 09/670096
DATED : March 31, 2009
INVENTOR(S) : Linda S. Mansfield et al.

Page 1 of 1

It is certified that error appears in the above--identified patent and that said Letters Patent is hereby corrected as shown below:

Column 4, line 38, "position" should be --portion--.

Column 4, line 56, "16(B±4)" should be --16(±4)--.

Column 5, line 9, "1 6 (±4)" should be --16 (±4)--.

Column 6, line 8, "In genera." should be --In general,--.

Column 8, line 44, "30 (35 4) kDa" should be --30 (±4) kDa--.

Column 8, line 55, "30 (35 4) kDa" should be --30 (±4) kDa--.

Column 9, line 10, "30 (35 4) kDa" should be --30 (±4) kDa--.

Column 9, line 55, "removing he" should be --removing the--.

Column 16, line 52, "0.100 units penicillin" should be --100 units penicillin--.

Column 16, line 65, "DMEN" should be --DMEM--.

Column 17, line 6, "are then placed into" should be --are then plated into--.

Column 21, line 11, "the bilt" should be --the bile--.

Signed and Sealed this

Eighteenth Day of August, 2009

David J. Kappos
*Director of the United States Patent and Trademark Office*